(12) United States Patent
Zhao

(10) Patent No.: US 10,744,486 B2
(45) Date of Patent: Aug. 18, 2020

(54) CATALYST SUPPORT MATERIALS AND CATALYST MATERIALS USEFUL FOR FISCHER-TROPSCH PROCESSES

(71) Applicant: CLARIANT CORPORATION, Louisville, KY (US)

(72) Inventor: Shizhong Zhao, Prospect, KY (US)

(73) Assignee: Clariant Corporation, Louisville, KY (US)

( * ) Notice: Subject to any disclaimer, the term of this patent is extended or adjusted under 35 U.S.C. 154(b) by 0 days.

(21) Appl. No.: 15/242,865

(22) Filed: Aug. 22, 2016

(65) Prior Publication Data

US 2017/0065963 A1    Mar. 9, 2017

Related U.S. Application Data

(60) Provisional application No. 62/214,418, filed on Sep. 4, 2015.

(51) Int. Cl.
*B01J 21/12* (2006.01)
*C10G 2/00* (2006.01)
(Continued)

(52) U.S. Cl.
CPC .......... *B01J 21/12* (2013.01); *B01J 23/8913* (2013.01); *B01J 35/023* (2013.01); *B01J 35/1014* (2013.01); *B01J 35/1019* (2013.01); *B01J 35/1038* (2013.01); *B01J 35/1042* (2013.01); *B01J 35/1061* (2013.01); *B01J 37/0045* (2013.01); *B01J 37/0201* (2013.01); *B01J 37/0203* (2013.01); *B01J 37/0205* (2013.01); *B01J 37/0207* (2013.01); *B01J 37/0215* (2013.01); *C07C 1/0435* (2013.01);
(Continued)

(58) Field of Classification Search
CPC ...... B01J 21/12; B01J 23/8913; B01J 35/023; B01J 35/1014; B01J 35/1019; B01J 35/1038; B01J 35/1042; B01J 35/1061; B01J 37/0045; B01J 37/0201; B01J 37/0203; B01J 37/0205; B01J 37/0207; B01J 37/0215; C07C 1/0435; C10G 2/33; C10G 2/332; C10G 2/333
See application file for complete search history.

(56) References Cited

U.S. PATENT DOCUMENTS 4,499,209 A    2/1985  Hoek
6,638,889 B1 * 10/2003  Van Berge ............... B01J 23/75
                                                     502/300

(Continued)

OTHER PUBLICATIONS

Anna Maria Venezia, Co/SiO2 catalysts for Fischer-tropsch synthesis; effect of Co loading and support modification by TiO2, Catalysis Today 197 (2012) 18-23.

(Continued)

*Primary Examiner* — Patricia L. Hailey
*Assistant Examiner* — Michael Forrest

(57) ABSTRACT

The present disclosure relates to catalyst support materials and cobalt catalyst materials including such support materials, and their uses in Fischer-Tropsch processes. In certain aspects, a catalyst support material includes alumina, silicon oxide and titanium dioxide. In other aspects, a catalyst material includes a catalyst support material as described herein, with a catalytic metal such as cobalt disposed thereon.

16 Claims, 1 Drawing Sheet

(51) Int. Cl.
  *B01J 23/89* (2006.01)
  *B01J 35/02* (2006.01)
  *B01J 35/10* (2006.01)
  *B01J 37/02* (2006.01)
  *B01J 37/00* (2006.01)
  *C07C 1/04* (2006.01)

(52) U.S. Cl.
  CPC ............... *C10G 2/33* (2013.01); *C10G 2/332* (2013.01); *C10G 2/333* (2013.01); *B01J 2523/00* (2013.01); *C07C 2523/89* (2013.01)

(56) References Cited

U.S. PATENT DOCUMENTS

| | | | |
|---|---|---|---|
| 6,875,720 B2 | 4/2005 | Van Berge | |
| 6,914,082 B2 | 7/2005 | Zhang | |
| 6,977,273 B2 | 12/2005 | Roy-Auberger | |
| 7,262,225 B2 | 8/2007 | Van Berg | |
| 7,341,976 B2 | 3/2008 | Espinoza | |
| 7,348,293 B2 * | 3/2008 | Timken | B01J 35/002 502/258 |
| 7,449,496 B2 | 11/2008 | Espinoza | |
| 7,811,967 B2 | 10/2010 | Reynhout | |
| 9,359,270 B2 | 6/2016 | Daly | |
| 2007/0270514 A1 * | 11/2007 | Lok | B01J 21/04 518/715 |
| 2008/0287556 A1 * | 11/2008 | Bellussi | B01J 23/75 518/715 |
| 2010/0022388 A1 | 1/2010 | Soled | |
| 2012/0190541 A1 * | 7/2012 | Koranne | B01J 21/063 502/439 |

OTHER PUBLICATIONS

Hinchiranan, Sukamon, et al., TiO2 promoted Co/SiO2 catalysts for Fischer-Tropsch synthesis, Fuel Processing Technology (2008, p. 455-459.

* cited by examiner

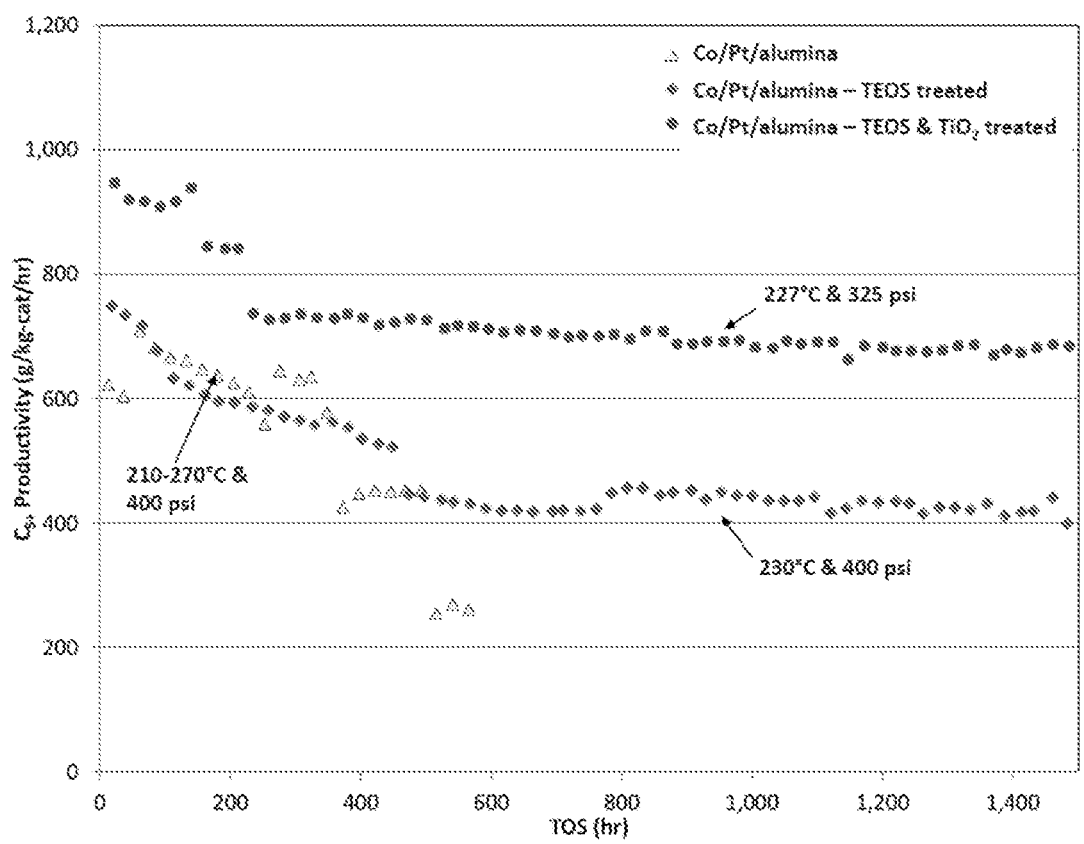

CATALYST SUPPORT MATERIALS AND CATALYST MATERIALS USEFUL FOR FISCHER-TROPSCH PROCESSES

CROSS-REFERENCE TO RELATED APPLICATIONS

This application claims priority to U.S. Provisional Patent Application Serial No. 62/214,418 filed Sep. 4, 2015, which is incorporated herein by reference in its entirety.

BACKGROUND OF THE DISCLOSURE

1. Field of the Disclosure

The present disclosure relates generally to catalyst support materials and catalyst materials. The present disclosure relates more particularly to catalyst support materials and cobalt catalyst materials including such support materials, and their uses in Fischer-Tropsch processes.

2. Technical Background

The Fischer-Tropsch process can be used for the conversion of synthesis gas ("syngas," a mixture of $H_2$ and CO) into liquid and/or solid hydrocarbons. The syngas can be made from a variety of feedstocks (e.g. natural gas, associated gas and/or coal-bed methane, biomass, residual oil fractions and coal). Fischer-Tropsch processes are conducted in a reactor in the presence of a suitable catalyst at elevated temperature and pressure to form paraffinic compounds ranging from methane to high molecular weight compounds comprising up to 200 carbon atoms, or, under particular circumstances, even more. Catalyst materials generally include an active component (e.g., a metal, often provided in the form of an oxide) supported on a catalyst support, which can be a porous refractory oxide such as alumina or silica. The support material can provide a high surface area upon which the active component can be dispersed and a pore network through which the reactant gases can diffuse in and the reaction products can diffuse out. The integrity and durability of the supporting material in the reaction conditions are very critical parameters for the use of the catalyst.

Catalyst materials become less active over time, via a variety of mechanisms. For example, the catalyst can be poisoned by a number of different species including, for example, sulfur, sodium, nitrogen or carbon containing compounds, all of which de-activate the catalyst. Moreover, the dispersion of the metal or metal component may decreases over time. Also, sintering and agglomeration of the support particles reduces the surface area of the support and consequently the activity of the catalyst. Catalyst materials can also break into smaller pieces, especially in fluidized processes, and become entrained in the gaseous effluent. Accordingly, catalyst materials are replaced periodically in order to maintain acceptable product yield.

Fischer-Tropsch processes can be carried out in a variety of types of reaction system; the type of reaction system will dictate the form of the catalyst material. Reactions carried out in fixed-bed reactors can be performed using catalyst pellets, made, for example, by conventional methods such as tableting and extrusion. Currently, the slurry bubble column reactor is commonly used for Fischer-Tropsch processes. Such processes use much smaller catalyst material particles, often substantially spherical in shape and made by spray-drying. The fluidized nature of processes conducted in slurry bubble column reactors requires the particulate catalyst used therein to have a relatively high mechanical strength in order to survive the many interparticle collisions. Moreover, Fischer-Tropsch synthesis in a slurry bubble column reactor exposes the catalyst material to high temperature, high water partial pressure, and acidic species; these features further affect the durability of the catalyst material.

Alumina is a conventional material for use as a support for cobalt-based Fischer-Tropsch catalyst materials, especially those used in slurry bubble column reactors. The alumina is typically provided in a transition form, such as gamma-alumina or theta-alumina, and formed in a shape suitable for the particular reaction system, spray-dried microspherical particles in the case of the slurry bubble column reactor. The active metal cobalt is loaded onto the alumina by conventional methods such as impregnation of a cobalt-containing precursor and calcining to form cobalt oxide. It has been found that under the conditions in a slurry bubble column reactor, the transition alumina support can be rehydrated to boehmite and dissolve in the Fischer-Tropsch synthesis products. This can cause deactivation of the catalyst material, difficulties in catalyst/product separation, deactivation of downstream catalysts and contamination of the products.

Thus, there remains a need to further improve the stability of catalytic support materials and catalytic material used in Fischer-Tropsch processes, especially for use in slurry bubble column reactors.

SUMMARY OF THE DISCLOSURE

In one aspect, the disclosure provides a catalyst support material comprising in the range of about 60 wt % to about 96 wt % alumina, calculated as $Al_2O_3$ on an oxide basis, in the range of about 1 wt % to about 20 wt % silicon oxide, calculated as $SiO_2$ on an oxide basis and in the range of about 1 wt % to about 20 wt % titanium dioxide, calculated as $TiO_2$ on an oxide basis. In certain embodiments, the the alumina and the silicon oxide are substantially coated by the titanium dioxide.

In another aspect, the disclosure provides a catalyst material comprising a catalyst support material as described herein and one or more catalytic metals (e.g., cobalt and one or more of platinum, ruthenium, rhenium, silver and boron) disposed on the catalyst support material.

In another aspect, the disclosure provides a process for producing one or more hydrocarbons, the process comprising contacting carbon monoxide and hydrogen with a catalyst material as described herein, for example, in a slurry bubble column reactor.

Other aspects and embodiments of the disclosure will be apparent in view of the following detailed description.

BRIEF DESCRIPTION OF THE DRAWINGS

FIG. 1 is a graph demonstrating long-term performance of a catalyst material of the disclosure and two comparative materials.

DETAILED DESCRIPTION

Before the disclosed processes and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the term "contacting" includes the physical contact of at least one substance to another substance.

All percentages, ratios and proportions herein are by weight, unless otherwise specified. A weight percent (weight %, also as wt %) of a component, unless specifically stated to the contrary, is based on the total weight of the formulation or composition in which the component is included (e.g., on the total amount of the catalyst material). All weight percent values are calculated on an oxide basis.

The inventors have determined that coating an alumina- and silicon oxide-containing support material with titanium oxide can result in catalyst materials having increased catalytic stability while retaining (at least) acceptable catalytic activity. While silicon oxide alone can be used to chemically stabilize an alumina support material, catalysts made using silicon oxide-stabilized support materials can be less catalytically active and less catalytically stable. The inventors have determined that addition of titanium oxide can improve the catalytic behavior while retaining chemical stability, so that the catalyst can be used for a longer lifetime, thus improving overall efficiency. Materials can be provided that have sufficient physical strength, pore structure, hydrothermal stability and catalytic stability to be used in Fischer-Tropsch processes conducted in slurry bubble column reactors.

Accordingly, one embodiment of the disclosure is a catalyst support material comprising alumina, silicon oxide and titanium dioxide. In certain embodiments, the alumina and the silicon oxide are substantially coated by the titanium dioxide.

The alumina can be provided in a variety of forms. The alumina can be provided, for example, substantially as a transition alumina. The transition alumina matrix may include an alumina phase selected from the group consisting of gamma-alumina; eta-alumina; delta alumina; theta-alumina, and any combinations of two or more thereof. In certain embodiments, the stabilized catalyst support preferably comprises a gamma alumina XRD pattern, but is different from a conventional gamma alumina in a way that the primary particles of the stabilized alumina support inherit the unique morphology and crystallite size of a boehmite material from which it is derived. Moreover, the catalyst support material preferably contains a gamma alumina phase or a gamma-like alumina phase, but does not contain another transitional alumina phase selected from the group consisting of delta alumina and theta alumina. Alternately or additionally, the catalyst support material prepared as described herein may include a transitional alumina phase other than gamma-alumina, such as delta-alumina and/or theta-alumina. In some embodiments, the catalyst support material may comprise an alpha alumina phase or an alpha-like alumina phase (e.g., when the method of preparation employs a heat treatment at a temperature greater than about 900° C.).

As the person of ordinary skill in the art will appreciate, the alumina has a nominal formula of $Al_2O_3$, but may in reality have a slightly different formula. Moreover, the alumina can, depending on processing conditions and environmental conditions, include minor amounts of hydration (e.g., less than 1%, or even less than 0.1% hydrate). Desirably, the alumina in the catalyst support material is substantially free of boehmite, bayerite, gibbsite, and diaspore (e.g., less than 1%, or even less than 0.1% total). As described in more detail below, however, it may be desirable to prepare the catalyst support materials using hydrated alumina such as boehmite or bayerite as starting materials. Moreover, the alumina may contain minor amounts of impurities, e.g., iron, silicon, sodium, nitride, sulfide). However, such impurities are desirably present in the alumina, if at all, in only very small amounts (e.g., less than 1 wt %, less than 0.5 wt %, less than 0.1 wt % or even less than 0.01 wt % total, on an oxide basis).

The alumina is the major component of the catalyst support material. For example, in one embodiment, the catalyst support material includes about 60 wt % to about 96 wt % alumina, calculated as $Al_2O_3$. In other various embodiments, the catalyst support material includes alumina in an amount of about 60 wt % to about 93 wt %, or about 60 wt % to about 90 wt %, or about 60 wt % to about 88 wt %, or about 60 wt % to about 85 wt %, or about 60 wt % to about 80 wt %, or about 65 wt % to about 96 wt %, or about 65 wt % to about 93 wt %, or about 65 wt % to about 90 wt %, or about 65 wt % to about 88 wt %, or about 65 wt % to about 85 wt %, or about 65 wt % to about 80 wt %, or about 70 wt % to about 96 wt %, or about 70 wt % to about 93 wt %, or about 70 wt % to about 90 wt %, or about 70 wt % to about 88 wt %, or about 70 wt % to about 85 wt %, or about 70 wt % to about 80 wt %, or about 75 wt % to about 96 wt %, or about 75 wt % to about 93 wt %, or about 75 wt % to about 90 wt %, or about 75 wt % to about 88 wt %, or about 75 wt % to about 85 wt %, or about 80 wt % to about 96 wt %, or about 80 wt % to about 93 wt %, or about 80 wt % to about 90 wt %, or about 80 wt % to about 88 wt %.

As the person of ordinary skill in the art will appreciate, the silicon oxide can be provided in a variety of forms. For example, the silicon oxide can be present as silicon dioxide, which has the nominal formula $SiO_2$, but may in reality have a somewhat different formula. The silicon oxide can also be present in the form of a silicon aluminosilicate, which can be considered herein as a mixture of the silicon oxide and alumina at an atomic level. Moreover, the silicon oxide may contain minor amounts of impurities, e.g., iron, sodium, nitride, sulfide). However, such impurities are desirably present in the silicon oxide, if at all, in only very small amounts (e.g., less than 1 wt %, less than 0.5 wt %, less than 0.1 wt % or even less than 0.01 wt % total, on an oxide basis). As described in more detail below, the silicon oxide can be made by treatment of alumina with a silicate precursor such as tetraethylorthosilicate, then calcining the precursor to silicon oxide. The silicon oxide can be, for example, substantially amorphous.

The silicon oxide can be disposed together with the alumina in a variety of ways. For example, in certain embodiments, the silicon oxide substantially coats the alumina, e.g., as a layer of silicon oxide or a layer of silicon aluminosilicate. That is, in such embodiments, the alumina is substantially enveloped by the silicon oxide (which in turn can be substantially coated by the titanium dioxide). In certain such embodiments, less than 15%, less than 10%, less than 5%, or even less than 1% of surface of the alumina is not covered by silicon oxide. In other embodiments, the silicon oxide is dispersed in the alumina, for example, as a dispersed silicon oxide phase or a dispersed phase of a silicon aluminate. In other embodiments, the silicon oxide is homogeneously mixed throughout the alumina phase, e.g., as a substantially homogeneous silicon aluminate.

In certain embodiments, the silicon oxide is present in the catalyst support material in an amount in the range of about 0.3 wt % to about 20 wt %, calculated as $SiO_2$ on an oxide basis. For example, in various embodiments, the silicon oxide is present in the catalyst support material in an amount in the range of about 0.3 wt % to about 18 wt %, or about 0.3 wt % to about 15 wt %, or about 0.3 wt % to about 13 wt %, or about 0.3 wt % to about 10 wt %, or about 0.3 wt % to about 8 wt %, or about 1 wt % to about 20 wt %, or about 1 wt % to about 18 wt %, or about 1 wt % to about 15 wt %, or about 1 wt % to about 13 wt %, or about 1 wt % to about 10 wt %, or about 1 wt % to about 8 wt %, or about 2 wt % to about 20 wt %, or about 2 wt % to about 18 wt %, or about 2 wt % to about 15 wt %, or about 2 wt % to about 13 wt %, or about 2 wt % to about 10 wt %, or about 2 wt % to about 8 wt %, or about 3 wt % to about 20 wt %, or about 3 wt % to about 18 wt %, or about 3 wt % to about 15 wt %, or about 3 wt % to about 13 wt %, or about 3 wt % to about 10 wt %, or about 3 wt % to about 8 wt %, or about 5 wt % to about 20 wt %, or about 5 wt % to about 18 wt %, or about 5 wt % to about 15 wt %, or about 5 wt % to about 13 wt %, or about 5 wt % to about 10 wt %, or about 5 wt % to about 8 wt %.

As described above, the titanium dioxide substantially coats the alumina and the silicon oxide. That is, the alumina and the silicon oxide are substantially enveloped by the titanium dioxide. In certain embodiments, less than 15%, less than 10%, less than 5%, or even less than 1% of the surface of the alumina and silicon oxide is not covered by the titanium oxide.

As the person of ordinary skill in the art will appreciate, titanium dioxide has the nominal formula $TiO_2$, but may in reality have a somewhat different formula. Moreover, the titanium oxide may contain minor amounts of impurities, e.g., iron, aluminum, silicon, sodium, nitride, sulfide). However, such impurities are desirably present in the titanium dioxide, if at all, in only very small amounts (e.g., less than 1 wt %, less than 0.5 wt %, less than 0.1 wt % or even less than 0.01 wt % total, on an oxide basis). As described in more detail below, the titanium dioxide can be made by treatment of an alumina/silicon oxide material with a titanium oxide precursor such as titanium lactate, then calcining the precursor to titanium oxide. The titanium dioxide may also be formed by combination of nanoparticulate titanium dioxide (e.g., a titanium dioxide) with an alumina/silicon oxide material. The titanium dioxide can be, for example, substantially amorphous, substantially in a rutile phase, or a mixture of the two.

In certain embodiments, the titanium dioxide is present in the catalyst support material in an amount in the range of about 1 wt % to about 20 wt %. For example, in various embodiments, the titanium dioxide is present in the catalyst support material in an amount in the range of about 1 wt % to about 18 wt %, or about 1 wt % to about 15 wt %, or about 1 wt % to about 13 wt %, or about 1 wt % to about 10 wt %, or about 1 wt % to about 8 wt %, or about 2 wt % to about 20 wt %, or about 2 wt % to about 18 wt %, or about 2 wt % to about 15 wt %, or about 2 wt % to about 13 wt %, or about 2 wt % to about 10 wt %, or about 2 wt % to about 8 wt %, or about 3 wt % to about 20 wt %, or about 3 wt % to about 18 wt %, or about 3 wt % to about 15 wt %, or about 3 wt % to about 13 wt %, or about 3 wt % to about 10 wt %, or about 3 wt % to about 8 wt %, or about 5 wt % to about 20 wt %, or about 5 wt % to about 18 wt %, or about 5 wt % to about 15 wt %, or about 5 wt % to about 13 wt %, or about 5 wt % to about 10 wt %, or about 5 wt % to about 8 wt %.

As described above, the catalyst support materials described herein include alumina, silicon oxide and titanium dioxide. In desirable embodiments, the catalyst support material includes at least about 90 wt % of alumina, silicon oxide and titanium dioxide. For example, in various embodiments, the catalyst support material includes at least about 95 wt %, at least about 95 wt %, at least about 99 wt %, at least about 99.5 wt %, or at least about 99.9 wt % of alumina, silicon oxide and titanium dioxide. In certain embodiments, the catalyst support material consists essentially of the alumina, the silicon oxide and the titanium dioxide.

The catalyst support material can be formed in a variety shapes. For example, for use in the fabrication of catalysts for fluidized or slurry systems, the catalyst support material can be formed as a plurality of discrete porous particles. The discrete porous particles can be formed in a variety of particle sizes and distributions. For example, in certain embodiments, the discrete particles have an average discrete particle size in the range of about 10 μm to about 200 μm. In various other embodiments, the discrete porous particles have an average discrete particle size in the range of about 10 μm to about 150 μm, about 10 μm to about 100 μm, or about 10 μm to about 80 μm, or about 20 μm to about 200 μm, or about 20 μm to about 150 μm, or about 20 μm to about 100 μm, or about 20 μm to about 80 μm, or about 30 μm to about 200 μm, or about 30 μm to about 150 μm, or about 30 μm to about 100 μm, or about 30 μm to about 90 μm, or about 30 μm to about 80 μm. The discrete porous articles can be, for example, substantially spheroidal in shape, as would result from a spray drying process. The person of ordinary skill in the art can tune the spray drying process (and other processes used in the manufacture) to provide the desired particle shape and size.

Of course, in other embodiments, the catalyst material can be formed in other shapes. For example, the catalyst material can be formed into shapes such as spheres, pellets, cylinders (hollow or otherwise), symmetrical or asymmetrical tri-quadrulobes, for example, using extrusion or tableting methods. Such catalyst materials may be suitable for use in fixed bed reactors. Catalyst materials may also be coated on to a substrate or support, such as a ceramic surface or an internal surface of a reactor.

The catalyst support materials described herein are desirably porous. The catalyst support materials may have an average pore size larger than about 4 nm, for example, in the range of about 4 nm to about 50 nm, about 4 nm to about 20 nm, or about 9 nm to about 20 nm. In alternate embodiments, the average pore size is larger than about 6 nm, for example, in ther range of about 6 nm to about 50 nm, or about 6 nm to about 20 nm. In some embodiments, the catalyst support material has a bimodal distribution of pore sizes with the two modes differing by at least about 1 nm, or by at least about 3 nm. One mode is preferably in the range of about 4 nm to about 20 nm, or about 6 nm to about 20 nm, while the other mode is in the range of about about 15 nm to about 50 nm, or in the range of about 20 nm to about 40 nm.

The catalyst support materials described herein can be provided with a variety of different pore volumes, depending, e.g., on the processes used for making them and the desired end use. For example, in certain embodiments, a catalyst material as described herein has a pore volume within the range of about 0.05 to about 1 cm$^3$/g, or about 0.1 to about 1 cm$^3$/g, or about 0.2 to about 1 cm$^3$/g, or about 0.3 to about 1 cm$^3$/g, or about 0.5 to about 1 cm$^3$/g, or about 0.05 to about 0.8 cm$^3$/g, or about 0.1 to about 0.8 cm$^3$/g, or about 0.2 to about 0.8 cm$^3$/g, or about 0.3 to about 0.8 cm$^3$/g, or about 0.5 to about 0.8 cm$^3$/g, or about 0.05 to about 0.5 cm$^3$/g, or about 0.1 to about 0.5 cm$^3$/g, or about 0.2 to about 0.5 cm$^3$/g. The person of ordinary skill in the art can, in view of the processes described herein, provide a desired pore volume to a catalyst support material. Pore volumes are measured by Hg porisometry, and provide the total volume or pores below 5000 Å in size. The person of ordinary skill in the art can, in view of the processes described herein, provide a desired pore volume to a catalyst support material.

Similarly, the catalyst support materials described herein can be provided with a variety of different surface areas, depending, e.g., on the processes used for making them and the desired end use. The surface areas are measured using the Brunauer-Emmett-Teller (BET) Surface Area method. In certain embodiments, a catalyst support material as described herein has a surface area within the range of from about 10 to about 300 m$^2$/g, or about 50 to about 300 m$^2$/g, or about 70 to about 300 m$^2$/g, or about 100 to about 300 m$^2$/g, or about 10 to about 200 m$^2$/g, or about 50 to about 200 m$^2$/g, or about 70 to about 200 m$^2$/g, or about 100 to about 200 m$^2$/g, or about 10 to about 150 m$^2$/g, or about 50 to about 150 m$^2$/g, or about 70 to about 150 m$^2$/g, or about 100 to about 150 m$^2$/g, or about 90 to about 130 m$^2$/g. The person of ordinary skill in the art can, in view of the processes described herein, provide a desired surface area to a catalyst support material.

The catalyst support material can be made using a variety of conventional techniques. For example, the alumina/silicon oxide component of the catalyst support material can be made using techniques described in U.S. Pat. no. 7,341,976, which is hereby incorporated herein by reference in its entirety. In certain embodiments, alumina or a precursor thereof is combined with silicon oxide or a precursor thereof, then the mixture is dried. The mixture can be shaped at the same time, e.g., through spray drying. The mixture is desirably heated or otherwise treated under conditions sufficient to convert the alumina (if necessary) to a transition alumina form, and to convert the silicon oxide precursor to silicon oxide. The alumina/silicon oxide component can then be contacted with titanium dioxide or a precursor thereof, then dried (calcining and/or shaping as necessary) to provide the catalyst support material.

For example, in one embodiment, the alumina or the precursor thereof is provided as a crystalline hydrous alumina precursor, such as bauxite, gibbsite or boehmite. In one particular embodiment, the alumina or the precursor thereof is provided as boehmite. In other embodiments, the alumina or the precursor thereof is provided as a transition alumina, e.g., gamma alumina. The transition alumina can be provided, for example, in substantially the same crystalline form as in the catalyst support material.

The crystalline hydrous alumina precursor may comprise at least one crystalline aluminum hydroxide. Crystalline aluminum hydroxides are precursors of metastable transition aluminas. Examples of crystalline aluminum hydroxides include gibbsite, bayerite, nordstrandite, diaspore, boehmite, and tohdite. The crystalline forms of aluminum trihydroxide are gibbsite ($Al(OH)_3$), bayerite (a polymorph of gibbsite), and nordstrandidte, whereas the crystalline forms of aluminum oxide hydroxide are boehmite (AlOOH) and diaspore. In certain embodiments, the crystalline hydrous alumina precursor includes at least one crystalline boehmite; or at least one crystalline bayerite; or a plurality thereof; or combinations thereof.

The crystalline hydrous alumina precursor is desirably provided as a solid form and does not substantially include a dissolved form, such as an aluminum salt or an aluminate salt. However, it is envisioned that the crystalline hydrous alumina precursor may include both solid and dissolved alumina precursor compounds, such as in a non-limiting example, the crystalline hydrous alumina precursor may include a mixture of solid particles of a crystalline aluminum hydroxide and dissolved alumina precursor compound (e.g., aluminate salt or dissolved aluminum salt or both) in a solvent.

The crystalline hydrous alumina precursor preferably has an average crystallite size selected from an optimum range. The higher the average crystallite size of crystalline hydrous alumina precursor, the better the hydrothermal resistance of the support, but the lower the surface area of the support. As the person of ordinary skill in the art will appreciate, there is a trade-off between desirability of hydrothermal resistance and requirement for a specific surface area needed for supporting catalytic metal(s) of the resulting stabilized supported catalyst. This trade-off may dictate an optimum range of average crystallite sizes from which an average crystallite size is selected so as to achieve a hydrothermal resistance and a surface area suitable for the end-use catalyst. The optimum range of average crystallite size may have a low limit determined by a desired minimum level of hydrothermal resistance of the resulting support (e.g., less than 10% change in the average pore size in a steaming test) and an upper limit determined by a desired minimum surface area or maximum average pore size (e.g., an average pore size of not more than about 20 nm; or a BET surface area of the support of at least about 50 m$^2$/g). The low limit optimum of the optimum range of average crystallite size may be determined by both a desired minimum level of hydrothermal resistance of the resulting support and a minimum average pore size (e.g., an average pore size greater than about 6 nm; or a BET surface area of the support of less than about 200 m$^2$/g).

In some embodiments, the crystalline hydrous alumina precursor may include (or even consist essentially of) one crystalline bayerite or a plurality of crystalline bayerites. The crystalline bayerite may have an average crystallite size ranging from about 30 nm to about 50 nm; or alternatively from about 35 nm to about 45 nm. When the crystalline hydrous alumina precursor comprises more than one crystalline bayerite, the plurality of crystalline bayerites preferably have an average crystallite size that differ by at least about 1 nanometer (nm), preferably by at least about 3 nanometer (nm); more preferably by at least about 5 nanometer (nm). Such a crystalline hydrous alumina precursor can be obtained as commercial bayerite. Commercial bayerite may be available as a powder primarily having micron-sizes, e.g., with particle sizes ranging between about 0.1 micron and about 50 microns. By way of example and not limitation, suitable commercial boehmites include bayerite from UOP LLC (Des Plaines, Ill.) under the trademark Versal™. A commercial bayerite may have an average particle size of less than about 40 microns, such as between about 20 microns and about 40 microns or between about 15 microns and about 30 microns. Without being limited, for powders obtained with an average particle size outside a desired range, the average particle size may be adjusted by spray-drying (e.g., shaping) a dispersion or suspension of the bayerite powder in a solvent (such as a bayerite sol or a bayerite slurry) so as to obtain a bayerite material with a desired average particle size and/or particle size distribution, for example as disclosed herein. It is to be understood that the desired average particle size and/or particle size distribution is generally dictated by the end use of the catalyst material made from the catalyst support material.

The crystalline hydrous alumina precursor may include (or even consist essentially of) one crystalline boehmite or a plurality of crystalline boehmites. The boehmite in the crystalline hydrous alumina precursor can be provided, for example, as synthetic boehmite. Synthetic boehmite includes any boehmite not derived from ore. When the boehmite is synthetic boehmite, the synthetic boehmite can be made by any suitable process. For example, synthetic boehmite can be made by a gellation method such as a modified Ziegler alcohol process that produces high purity gels derived from aluminum metal or a process comprising dissolving and precipitating aluminum trihydrate that produces high porosity gels albeit with more impurities. For instance, maturation of an $Al(OH)_3$ gel at pH>12 and 80° C. produces synthetic boehmite. The maturation time of the $Al(OH)_3$ gel affects the average crystallite size of the resulting synthetic boehmite, as typically the longer the maturation, the larger the average crystallite size of the resulting synthetic boehmite. High purity boehmite gels may contain very low levels (i.e., less than 0.01 wt %) of impurities typically present in alumina, such as iron, silicon, and sodium. High purity boehmite gels have a structure that consists of small boehmite crystals, often referred to as pseudoboehmite, which is in the form of aluminum monohydrate, $AlO(OH)$—$H_2O$. In alternative embodiments, the boehmite in the crystalline hydrous alumina precursor can be derived from natural boehmite. In one alternative embodiment, any conventional natural boehmite may be suitable as the boehmite. Minor variations, such as in impurities, may exist between various commercial sources of natural boehmite. Exemplary impurities include, for example, elements or compounds derived from other materials contained in natural sources of boehmite. Thus, natural boehmite may include minor amounts of any one or combination of iron, titanium, and silicon. According to some embodiments, the crystalline hydrous alumina precursor can be a mixture of a synthetic boehmite and a natural boehmite. According to other embodiments, the crystalline hydrous alumina precursor can be a mixture of two or more synthetic boehmites differing in average crystalline sizes by at least about 1 nm.

As described above, the crystalline hydrous alumina precursor may comprise one crystalline boehmite or a plurality of crystalline boehmites. When the crystalline hydrous alumina precursor comprises more than one crystalline boehmite, the plurality of crystalline boehmites preferably have an average crystallite size that differ by at least about 1 nanometer (nm).

The average crystallite size of crystalline boehmite or bayerite may be determined by X-ray diffraction (XRD) patterns of the boehmite material. XRD sizing of crystallites may be performed using the Scherrer equation (see for example H. P. Klug and L. E. Alexander, X-Ray Diffraction Procedures for Polycrystalline and Amorphous Materials, John Wiley, New York, 2nd Edition, 1974).

The crystalline hydrous alumina precursor can be obtained as commercial boehmite. Commercial boehmite may be available as a powder primarily having micron-sizes, e.g., with particle sizes ranging between about 1 and about 50 microns. A commercial boehmite may have an average particle size of less than about 40 microns, such as between about 20 microns and about 40 microns or between about 15 microns and about 30 microns. Without being limited, for powders obtained with an average particle size outside a desired range, the average particle size may be adjusted by spray-drying (shaping) a dispersion or suspension of the boehmite powder in a solvent (such as a boehmite sol or a boehmite slurry) so as to obtain a boehmite material with a desired average particle size and/or particle size distribution, for example as disclosed herein. It is to be understood that the desired average particle size and/or particle size distribution may be dictated by the end use of the catalyst made from the stabilized support. In some embodiments, the boehmite sol or a boehmite slurry may further contain an acid (such as nitric acid, acetic acid, and the like) so as to form a colloidal suspension of the boehmite material before re-shaping. In alternate embodiments, the boehmite sol or slurry does not contain an acid before re-shaping.

By way of example and not limitation, suitable commercial boehmites include boehmites from Sasol North America Inc. (Houston, Tex.) under the registered trademarks Dispal® owned by Sasol North America Inc. (Houston, Tex.) and Disperal® owned by Sasol Germany GMBH (Hamburg, Germany); boehmites from Almatis Adsorbents & Catalysts, Inc. (Leetsdale, Pa.) under the registered trademark Hi Q®; and high-purity boehmite powder from WesBond Corporation (Wilmington, Del.) under the tradename Wesolok.

The crystalline hydrous alumina precursor may be available in a variety of rheological and physical forms. For instance, the crystalline hydrous alumina precursor may be in the form of a powder, a gel, a sol, a slurry, or a paste. A boehmite "sol" refers to a two-phase colloidal system where the continuous phase is liquid and the dispersed phase (i.e., boehmite) is solid. A boehmite "sol" may comprise nano-sized particles of boehmite, such as varying between about 10 and about 1000 nm. If the solid particles aggregate or polymerize to form a giant aggregate that extends through the sol, the boehmite material is said to be a "gel." A boehmite "sol" may be transformed into a "gel" and sometimes vice versa. One property of the boehmite powders is that a particle size reduction can be obtained by chemical attack such as in the presence of a dilute monovalent acid. For example, to form a "sol", boehmite particles in a powder break down due to chemical attack by the acid into smaller fragments, which additionally are provided with a positive charge. The positively-charged fragments in the "sol" may not settle in the continuous phase due to electrostatic repulsion. A boehmite "slurry" refers to a boehmite powder dispersed in a solvent. In an embodiment, a boehmite "slurry" comprises a boehmite powder with larger particle sizes than that of a colloidal state of boehmite in a "sol." A boehmite "slurry" typically comprises micron-sized particles of boehmite. A boehmite "sol" or "slurry" may comprise less than about 50% by weight of solids, preferably between about 20 wt % and about 45 wt % solids, more preferably between about 20 wt % and about 40 wt % solids. A boehmite "paste" refers to a boehmite powder mixed with a small amount of solvent. Generally, a boehmite paste may comprise more than about 80% by weight of solids, preferably between about 80 wt % and about 95 wt % solids, more preferably between about 85 wt % and about 95 wt % solids.

The selection of the average crystallite size for the crystalline hydrous alumina precursor is preferably dictated by a desired resistance to hydrothermal degradation of the resulting stabilized support and a desired porosity (e.g., surface area, average pore size, and the like) to provide a suitable surface to deposit catalytic metal(s). The higher the average crystallite size of a crystalline boehmite, the better the hydrothermal resistance to the alumina matrix derived therefrom. It is expected that the average crystalline size of other crystalline hydrous alumina precursors, such as bayerite, gibbsite, and diaspore, would also have an optimum range to provide the desired hydrothermally stable support with a suitable porosity. The low limit of the average crystallite size optimum range may be dictated by a minimum resistance to hydrothermal degradation (e.g., steam resistance); alternatively or additionally, by a maximum surface area and/or minimum average pore size that may be achieved in the stabilized support. The upper limit of the average crystallite size optimum range may be dictated by a minimum surface area and/or a maximum average pore size.

In some embodiments, the crystalline hydrous alumina precursor comprises more than about 75 percent by weight of one crystalline boehmite. In alternate embodiments, the crystalline hydrous alumina precursor comprises more than about 80 percent by weight of one crystalline boehmite.

In other embodiments, the crystalline hydrous alumina precursor comprises two or more crystalline boehmites differing in average crystallite size. When a mixture of boehmites with various average crystallite sizes is used, the mixture of boehmites may comprise a first boehmite having a first average crystallite size and a second boehmite having a second average crystallite size, wherein the first average crystallite size is at least about 1 nm smaller, preferably at least about 3 nm smaller, more preferably at least about 5 nm smaller, than the second average crystallite size. The proportion of the at least two boehmites with different average crystallite sizes depends on the desired properties of stabilized aluminum oxide porous structure, as described, for example, in U.S. Pat. No. 7,341,976, which is hereby incorporated herein by reference in its entirety.

The alumina or the precursor thereof can be pretreated before it is combined with the silicon oxide or the precursor thereof. For example, the alumina or the precursor thereof can be spray dried, shaped (e.g., via pelletizing or extrusion using conventional additives and techniques), and/or heat treated before being combined with the silicon oxide or the precursor thereof. If the alumina or the precursor thereof is provided as a crystalline hydrous alumina precursor, it can be desirable to heat treat it at temperatures less than that necessary to convert the precursor to alumina. Heat treatment can advantageously render substantially non-dispersible any water-dispersible content in the alumina precursor. For example, a boehmite or bayerite precursor can be heated at a temperature in the range of about 250 C. to about 350 C., desirably in an oxidizing atmosphere, to render it substantially non-dispersible in aqueous media.

The silicon oxide of the precursor thereof can be provided in many forms. For example, the silicon oxide or the precursor thereof can be provided as nanoparticulate silica, e.g., as a colloidal silica suspension. Commercial sources of colloidal silicas are available from Grace Davison (Columbia, Md.) under the Trademark Ludox®; and from WesBond Corporation (Wilmington, Del.) under the Trademarks Megasol® and Nyacol®. The silicon oxide or the precursor thereof can alternatively be provided as an compound of silicon like a silane or siloxane, such as tetraethylorthosilicate. Other suitable compounds of silicon include ammonium silicate [e.g., of formula $(SiO_2)_x \cdot (NH_4)_2O$ with x between 2 and 6], sodium silicate ($Na_2Si_3O_7$), calcium silicate ($CaSiO_3$), tetraalkyl orthosilicate (e.g, tetramethyl orthosilicate, tetraethyl orthosilicate, tetrapropyl orthosilicate, tetraisopropyl orthosilicate, tetrabutyl orthosilicate, tetrahexyl orthosilicate, tetraallyl orthosilicate), silicon tetraboride ($SiB_4$), silicon tetraacetate ($Si(OCOCH_3)_4$,), zirconium silicate ($ZrSiO_4$), silicic acid ($H_2O_3Si$), or a silica-alumina gel.

The silicon oxide or the precursor thereof may be combined with the alumina or the precursor thereof in a variety of fashions, e.g., by combining them together in a suitable solvent as a solution or slurry. The alumina or the precursor thereof and the silicon oxide or the precursor thereof can each be soluble (e.g., dissolved in the solvent) in said solvent; alternatively, they may each be insoluble in said solvent (e.g., in the form of small solid particles suspended or dispersed in the solvent). The mixture so formed can thus be in the form of a slurry or a sol.

The mixture of the silicon oxide or the precursor thereof with the alumina or the precursor thereof is then dried to form an alumina/silicon oxide composition. The mixture can also be shaped to a desired shape, such as particles of a size suitable for use in fluidized or slurried applications as described above, or extrudates or tablets for use in fixed bed applications. Thus, the mixture can be spray dried, tableted or extruded to form a desired shape.

In many embodiments, the mixture the silicon oxide or the precursor thereof with the alumina or the precursor thereof is calcined to form the alumina/silicon oxide composition. Depending on the temperature, calcination can convert an alumina precursor such as a hydrous alumina to a transition alumina, such as gamma alumina, and convert a silicon oxide composition, e.g., tetraethylorthosilicate, to silicon oxide. Calcining can also remove any solvent or other organic material remaining from an earlier process step. Calcining is a heat treatment at an elevated temperature of at least about 200° C. in an oxidizing environment (such as air). In certain embodiments, the mixture is calcined at a temperature of about 450° C. or higher, e.g., a temperature of about 500° C. or higher, or a temperature of about 600° C. or higher. In certain embodiments, the calcining is performed at a temperature of less than about 900° C., less than about 850° C. In other alternative embodiments, the calcining is performed at a temperature between about 900° C. and about 1600° C., or between about 1000° C. and about 1500° C. In some embodiments, the mixture is dried and/or shaped before calcining.

It is to be understood that the dehydration of the mixture (e.g., by calcination) may produce a certain distribution of pores in the resulting catalyst support material. Some interparticle pores are developed from the packing of the particles of the alumina or the precursor thereof (i.e., spaces in between the particles), while other pores are formed by the loss of water from crystals of a crystalline hydrous alumina precursor such as alumina hydroxide or alumina monohydrate. Without being limited by theory, the volume and size of the interparticle pores may be directly dependent on the size of the alumina/precursor particles in the powder, and there may be a good correlation between the average crystallite size of the crystalline hydrous alumina precursor and the average pore size as described in U.S. Pat. No. 7,341, 976. Pore size control can therefore be affected by the selection of an optimum average particle size of the alumina/precursor or the use of a mixture of two or more alumina/precursors having different particle sizes, as well as by the calcination conditions. Without limitation, examples of suitable calcination conditions include the selected calcination temperature; the holding time at the selected calcination temperature; the heating ramp (e.g., 1-10° C/min) to the selected calcination temperature; the use of steam during calcination (or not using steam during calcination); calcination at atmospheric pressure or above or under vacuum. A pore regulating agent can also be used, as described in U.S. Pat. No. 7,341,976.

The alumina/silicon oxide composition is then combined with titanium dioxide or a precursor thereof. The titanium dioxide or the precursor thereof can be provided in many forms. For example, the titanium dioxide or the precursor thereof can be provided as nanoparticulate titanium dioxide, e.g., as a colloidal titanium dioxide suspension. The silicon oxide or the precursor thereof can alternatively be provided as an compound of titanium, e.g., a tetraalkyl orthotitanate (e.g., titanium isopropoxide) or a titanium salt such as titanium acetate or titanium lactate. The titanium dioxide or the precursor thereof can be combined with the alumina/silicon oxide composition, for example, in a suspension or slurry in a solvent. The mixture can then be dried. The mixture can optionally be shaped. For example, if the alumina/silicon oxide composition is not shaped as desired, the mixture of the alumina/silicon oxide composition with the titanium dioxide or precursor thereof can be shaped as desired, e.g., by spray-drying, extrusion or tableting.

In many embodiments, the mixture of the titanium dioxide or the precursor thereof with the alumina/silicon oxide composition is calcined to form the catalyst support material. Calcination can convert a titanium dioxide precursor to titanium dioxide. If calcination is not used in making the alumina/silicon oxide composition, the calcination can also convert an alumina precursor such as a hydrous alumina to a transition alumina, such as gamma alumina, and convert a silicon oxide composition, e.g., tetraethylorthosilicate, to silicon oxide. Calcining can also remove any solvent or other organic material remaining from an earlier process step. In certain embodiments, the mixture is calcined at a temperature of about 450° C. or higher, e.g., a temperature of about 500° C. or higher, or a temperature of about 600° C. or higher. In certain embodiments, the calcining is performed at a temperature of less than about 900° C., less than about 850° C. In other alternative embodiments, the calcining is performed at a temperature between about 900° C. and about 1600° C., or between about 1000° C. and about 1500° C. In some embodiments, the mixture is dried and/or shaped before calcining.

Another aspect of the disclosure is a catalyst material that includes a catalyst support material as described herein, and one or more catalytic metals disposed on the catalyst support material. The catalyst material may further include one or more promoters to modify the catalytic activity of the catalytic metal(s). In certain embodiments, the catalytic metal is a Fischer-Tropsch catalytic metal. In certain embodiments, the catalytic metal is selected from among the Group 8 elements of the Periodic Table, such as iron (Fe), ruthenium (Ru), and osmium (Os); Group 9 elements, such as cobalt (Co), rhodium (Rh), and iridium (Ir); Group 10 elements, such as nickel (Ni), palladium (Pd), and platinum (Pt); and the metals molybdenum (Mo), rhenium (Re), and tungsten (W). For example, in one embodiment, the catalytic metal is cobalt, iron, ruthenium, nickel, or a combination thereof. In another embodiment, the catalytic metal is cobalt, iron, ruthenium, or a combination thereof. In certain particular embodiments, the catalytic metal includes cobalt. For example, in one embodiment, the catalytic metal includes cobalt in combination with one or more of platinum, ruthenium, rhenium, silver and boron. The catalyst material desirably contains a catalytically effective amount of the catalytic metal(s). As the person of ordinary skill in the art will appreciate, the amount of catalytic metal(s) present in the catalyst may vary widely.

The total amount of the catalytic metal(s) and any promoters is desirably in the range of about 1 wt % to about 70 wt % of the total catalyst material. In certain embodiments, the total amount of the catalytic metal(s) and any promoters present in the catalyst material is in the range of about 1 wt % to about 60 wt %, or about 1 wt % to about 55 wt %, or about 1 wt % to about 50 wt %, or about 1 wt % to about 40 wt %, or about 1 wt % to about 37 wt %, or about 1 wt % to about 35 wt %, or about 2 wt % to about 70 wt %, or about 2 wt % to about 60 wt %, or about 2 wt % to about 50 wt %, or about 2 wt % to about 40 wt %, or about 2 wt % to about 37 wt %, or about 2 wt % to about 35 wt %, or about 5 wt % to about 70 wt %, or about 5 wt % to about 60 wt %, or about 5 wt % to about 50 wt %, or about 5 wt % to about 40 wt %, or about 5 wt % to about 37 wt %, or about 5 wt % to about 35 wt %, or about 10 wt % to about 70 wt %, or about 10 wt % to about 60 wt %, or about 10 wt % to about 50 wt %, or about 10 wt % to about 40 wt %, or about 10 wt % to about 37 wt %, or about 10 wt % to about 35 wt % (i.e., calculated on an oxide basis).

For example, when cobalt is included as a catalytic metal, the catalyst desirably includes cobalt in an amount totaling from about 1% to about 70% by weight (on an oxide basis) of total catalyst material. In certain embodiments, the total amount of the cobalt in the catalyst material is in the range of about 1 wt % to about 60 wt %, or about 1 wt % to about 55 wt %, or about 1 wt % to about 50 wt %, or about 1 wt % to about 40 wt %, or about 1 wt % to about 37 wt %, or about 1 wt % to about 35 wt %, or about 2 wt % to about 70 wt %, or about 2 wt % to about 60 wt %, or about 2 wt % to about 50 wt %, or about 2 wt % to about 40 wt %, or about 2 wt % to about 37 wt %, or about 2 wt % to about 35 wt %, or about 5 wt % to about 70 wt %, or about 5 wt % to about 60 wt %, or about 5 wt % to about 50 wt %, or about 5 wt % to about 40 wt %, or about 5 wt % to about 37 wt %, or about 5 wt % to about 35 wt %, or about 10 wt % to about 70 wt %, or about 10 wt % to about 60 wt %, or about 10 wt % to about 50 wt %, or about 10 wt % to about 40 wt %, or about 10 wt % to about 37 wt %, or about 10 wt % to about 35 wt % (i.e., calculated on an oxide basis).

In other embodiments, the catalytic metal can be iron or ruthenium, present, for example, in an amount as described above with respect to cobalt.

The person of ordinary skill in the art will appreciate that the catalytic metal is desirably in a substantially reduced state at the time of use in a Fischer-Tropsch synthesis. However, it will be understood that the catalytic metal can be present in the form of a metal compound, such as a metal oxide, a metal hydroxide, and the like. Oxide and/or hydroxide forms can be especially convenient for synthesis, transport and storage of the catalyst material. Reduction to reduced state can be performed in situ as a step in the Fischer-Tropsch synthesis process itself.

Optionally, the catalyst materials described herein can also include at least one promoter known to those skilled in the art. The promoter may vary according to the catalytic metal. A promoter can be an element that also, in an active form, has catalytic activity in the absence of the catalytic metal. Such an element will be termed herein a promoter when it is present in the catalyst in a lesser wt % than the catalytic metal.

A promoter preferably enhances the performance of the catalyst. Suitable measures of the performance that may be enhanced include selectivity, activity, stability, lifetime, reducibility and resistance to potential poisoning by impurities such as sulfur, nitrogen, and oxygen. A promoter is desirably a Fischer-Tropsch promoter, which is an element or compound that enhances the performance of a Fischer-Tropsch catalyst in a Fischer-Tropsch process.

It will be understood that as contemplated herein an enhanced performance of a promoted catalyst can be calculated according to any suitable method known to one of ordinary skill in the art. In particular, an enhanced performance can be given as a percent and computed as the ratio of the performance difference to the performance of a reference catalyst. The performance difference is between the performance of the promoted catalyst and the reference catalyst, wherein the reference catalyst is a similar corresponding catalyst having the nominally same amounts, e.g. by weight percent, of all components except the promoter. It will further be understood that as contemplated herein a performance can be measured in any suitable units. For example, when the performance is productivity, productivity can be measured in grams product per hour per liter reactor volume, grams product per hour per kilogram catalyst, and the like.

Suitable promoters vary with the catalytic metal and can be selected from Groups 1-15 of the Periodic Table of the Elements. A promoter can be in elemental form. Alternatively, a promoter can be present in an oxide compound. Further, a promoter can be present in an alloy containing the catalytic metal. Except as otherwise specified herein, a promoter is preferably present in an amount to provide a weight ratio of elemental promoter:elemental catalytic metal of from about 0.00005:1 to about 0.5:1, preferably from about 0.0005:1 to about 0.25:1 (dry basis). When the promoter comprises a metal from Groups 7, 8, 9, and 10 of the Periodic Table such as rhenium, ruthenium, platinum, or palladium, the weight ratio of elemental promoter:elemental catalytic metal may be between about 0.00005:1 and about 0.05:1.

Further, when the catalytic metal is cobalt or iron, suitable promoters include Group 1 elements such as potassium (K), lithium (Li), sodium (Na), and cesium (Cs); Group 2 elements such as calcium (Ca), magnesium (Mg), strontium (Sr), and barium (Ba); Group 3 elements such as scandium (Sc), yttrium (Y), and lanthanum (La); Group 4 elements such as titanium (Ti), zirconium (Zr), and hafnium (Hf); Group 5 elements such as vanadium (V), niobium (Nb), and tantalum (Ta); Group 6 elements such as molybdenum (Mo) and tungsten (W); Group 7 elements such as rhenium (Re) and manganese (Mn); Group 8 elements such as ruthenium (Ru) and osmium (Os); Group 9 elements such as rhodium (Rd) and iridium (fr); Group 10 elements such as platinum (Pt) and palladium (Pd); Group 11 elements such as silver (Ag) and copper (Cu); Group 12 elements such as zinc (Zn), cadmium (Cd), and mercury (Hg); Group 13 elements such as gallium (Ga), indium (In), thallium (Tl), and boron (B); Group 14 elements such as tin (Sn) and lead (Pb); and Group 15 elements such as phosphorus (P), bismuth (Bi), and antimony (Sb).

When the catalytic metal is cobalt, iron, or combinations thereof, the promoter can be selected from, for example, platinum, palladium, ruthenium, rhenium, silver, boron, copper, lithium, sodium, potassium, magnesium, manganese, or combinations thereof.

In certain embodiments, when the catalytic metal is cobalt, the promoter is rhenium, ruthenium, platinum, palladium, boron, silver, or a combination thereof. When the promoter includes rhenium, the rhenium can be present in the catalyst material in an amount, for example, between about 0.001 and about 5% by weight, between about 0.01 and about 2% by weight, or between about 0.2 and about 1% by weight. When the promoter includes ruthenium, the ruthenium can be present in the catalyst material, for example, in an amount between about 0.0001 and about 5% by weight, between about 0.001 and about 1% by weight, or between about 0.01 and about 1% by weight. When the promoter includes platinum, the platinum can be present in the catalyst material, for example, in an amount between about 0.00001 and about 5% by weight, more preferably between about 0.0001 and about 1% by weight, and most preferably between about 0.0005 and about 1% by weight. When the promoter includes palladium, the palladium can be present in the catalyst material, for example, in an amount between about 0.00001 and about 5% by weight, between about 0.0001 and about 2% by weight, or between about 0.0005 and about 1% by weight. When the promoter includes silver, the silver can be present in an amount, for example, from about 0.01 to about 10 wt % silver, from about 0.07 to about 7 wt % silver, or about 0.1 to about 5 wt % silver. When the promoter includes boron, the boron can be present in the catalyst material, for example, in an amount of from about 0.025 to about 2 wt % boron, from about 0.05 to about 1.8 wt % boron, or from about 0.075 to about 1.5 wt % boron.

By way of example and not limitation, when the catalytic metal is iron, suitable promoters include copper (Cu), potassium (K), silicon (Si), zirconium (Zr), silver (Ag), lithium (Li), sodium (Na), rubidium (Rb), cesium (Cs), magnesium (Mg), manganese (Mn), calcium (Ca), strontium (Sr), and barium (Ba). In certain embodiments, when the catalytic metal is iron, the promoter can include potassium, copper, lithium, sodium, silver, magnesium, or combinations thereof. When the catalytic metal is iron, the catalyst may include potassium or lithium as a promoter; and alternatively or in combination, the catalyst may include copper or silver. When the catalyst material comprises lithium as a promoter, lithium can be present, for example, in an amount between about 0.05 wt % and about 5 wt % of lithium, or between about 0.5 wt % and about 2 wt %. When the catalyst material includes silver as a promoter, silver can be present, for example, in an amount between about 0.001 wt % and about 5 wt % of silver; or between about 0.001 wt % and about 2 wt % of silver; or between about 0.005 wt % and 1 wt % of silver. When the catalyst material includes potassium as a promoter, potassium can be present, for example, in an amount between about 0.0001 wt % and about 10 wt % of potassium; or between about 0.0005 wt % and about 1 wt % of potassium; or between about 0.0005 wt % and about 0.5 wt % of potassium. When the catalyst material comprises calcium as a promoter, calcium can be present, for example, in an amount between about 0.001 wt % and about 4 wt % of calcium; or between about 0.5 wt % and about 3 wt % of calcium. When the catalyst material comprises copper as a promoter, copper can be present, for example, in an amount between about 0.1 wt % and about 10 wt % copper.

Alternatively, by way of example and not limitation, when the catalytic metal is ruthenium, suitable promoters include rhenium. When the ruthenium catalyst includes rhenium, the rhenium can be present, for example, in the catalyst material in an amount between about 0.001 and about 1% by weight, or between about 0.01 and about 0.5% by weight, or between about 0.05 and about 0.5% by weight.

The catalyst materials may be prepared using the catalyst support materials described herein using any suitable method. Without limitation, examples of suitable methods include impregnating a catalytic metal onto the catalyst support material as described herein, extruding the catalyst support material with the catalytic metal to prepare catalyst extrudates, spray-drying the catalytic metal and the catalyst support material from a liquid medium containing both, and/or precipitating the catalytic metal onto the catalyst support material. The catalyst materials may be used in the form of powders, particles, pellets, monoliths, honeycombs, packed beds, foams, and aerogels. The most preferred method of preparation may vary among those skilled in the art depending, for example, on the desired catalyst particle size. Those skilled in the art are able to select the most suitable method for a given set of requirements.

The catalyst materials described herein are desirably porous. The catalyst support materials may have an average pore size larger than about 4 nm, for example, in the range of about 4 nm to about 50 nm, about 4 nm to about 20 nm, or about 9 nm to about 20 nm. In alternate embodiments, the average pore size is larger than about 6 nm, for example, in ther range of about 6 nm to about 50 nm, or about 6 nm to about 20 nm. In some embodiments, the catalyst material has a bimodal distribution of pore sizes with the two modes differing by at least about 1 nm, or by at least about 3 nm. One mode is preferably in the range of about 4 nm to about 20 nm, or about 6 nm to about 20 nm, while the other mode is in the range of about about 15 nm to about 50 nm, or in the range of about 20 nm to about 40 nm.

The catalyst materials described herein can be provided with a variety of different pore volumes, depending, e.g., on the processes used for making them and the desired end use. For example, in certain embodiments, a catalyst as described herein has a pore volume within the range of about 0.05 to about 1 $cm^3/g$, or about 0.1 to about 1 $cm^3/g$, or about 0.2 to about 1 $cm^3/g$, or about 0.05 to about 0.8 $cm^3/g$, or about 0.1 to about 0.8 $cm^3/g$, or about 0.2 to about 0.8 $cm^3/g$, or about 0.05 to about 0.5 $cm^3/g$, or about 0.1 to about 0.5 $cm^3/g$, or about 0.2 to about 0.5 $cm^3/g$, or about 0.05 to about 0.3 $cm^3/g$, or about 0.1 to about 0.3 $cm^3/g$. The person of ordinary skill in the art can, in view of the processes described herein, provide a desired pore volume to a catalyst material. Pore volumes are measured by Hg porisometry, and provide the total volume or pores below 5000 Å in size. The person of ordinary skill in the art can, in view of the processes described herein, provide a desired pore volume to a catalyst material.

Similarly, the catalyst materials described herein can be provided with a variety of different surface areas, depending, e.g., on the processes used for making them and the desired end use. The surface areas are measured using the Brunauer-Emmett-Teller (BET) Surface Area method. In certain embodiments, a catalyst material as described herein has a surface area within the range of from about 10 to about 300 $m^2/g$, or about 20 to about 300 $m^2/g$, or about 50 to about 300 $m^2/g$, or about 10 to about 150 $m^2/g$, or about 20 to about 150 $m^2/g$, or about 50 to about 150 $m^2/g$, or about 10 to about 100 $m^2/g$, or about 20 to about 100 $m^2/g$, or about 50 to about 100 $m^2/g$, or about 60 to about 80 $m^2/g$. The person of ordinary skill in the art can, in view of the processes described herein, provide a desired surface area to a catalyst material.

One method of preparing a catalyst material includes applying a catalytic metal and/or promoter element onto the catalyst support material described herein. The applying step may include impregnating the catalyst support material with a solution containing the catalytic metal and/or promoter. Suitable solvents include water and organic solvents (e.g., toluene, methanol, ethanol, and the like). Those skilled in the art will be able to select the most suitable solvent for a given catalyst material. The catalytic metal and/or promoter can be in the form of a salt of a catalytic metal or promoter element. Thus, one method of preparing the catalyst includes incipient wetness impregnation of the catalyst support material with a solution of a soluble catalytic metal salt and optionally a soluble promoter metal compound. Incipient wetness impregnation preferably proceeds by dissolution of a compound (such as a cobalt compound) in a minimal amount of solvent sufficient to fill the pores of the support. Alternatively, the catalyst material can be applied to the stabilized support in the form of a zero-valent compound of a catalytic metal or promoter element. Thus, another method comprises impregnating the catalyst support material with a solution of zero-valent metal such as cobalt carbonyl (e.g., $Co_2(CO)_8$, $Co_4(CO)_{12}$) or the like. Multiple steps of impregnation can be done to achieve the desired loading level.

Another method of preparing the catalyst material includes impregnating the catalyst support material with a molten salt of a catalytic metal and/or promoter. One such method includes impregnating the support with a molten metal nitrate (e.g., $Co\ (NO_3)_2.6H_2O$). A promoter compound can be impregnated separately from any cobalt, in a separate step. Alternatively, a promoter compound can be impregnated simultaneously with, e.g. in the same solution as, at least a portion of the catalytic metal.

When a catalytic metal or promoter is impregnated as a salt or a zero valent compound, those skilled in the art will be able to select suitable such compound(s).

By way of example and not limitation, suitable cobalt-containing compounds include, for example, hydrated cobalt nitrate (e.g. cobalt nitrate hexahydrate), cobalt carbonyl, cobalt acetate, cobalt acetylacetonate, cobalt oxalate, and the like. Hydrated cobalt nitrate, cobalt carbonyl and cobalt acetate are exemplary of cobalt-containing compounds soluble in water. Cobalt oxalate is soluble in acids or acidic solutions. Cobalt acetate and cobalt acetylacetonate are exemplary of cobalt-containing precursor compounds soluble in an organic solvent.

Suitable rhenium-containing compounds soluble in water include, for example, perrhenic acid, ammonium perrhenate, rhenium pentacarbonyl chloride, rhenium carbonyl, and the like. Suitable ruthenium-containing precursor compounds soluble in water include for example ruthenium carbonyl, $Ru(NH_3)_6.Cl_3$, Ru(III)2,4-pentanedionate, ruthenium nitrosyl nitrate, and the like. Suitable platinum-containing precursor compounds soluble in water include, for example, $Pt(NH_3)_4(NO_3)_2$ and the like. Alternatively, the platinum-containing precursor can be soluble in an organic solvent, such as platinum acetyl acetonate soluble in acetone. Suitable boron-containing precursor compounds soluble in water include, for example, boric acid and the like. Alternatively, the boron-containing precursor can be soluble in an organic solvent. Suitable silver-containing precursor compounds soluble in water include, for example, silver nitrate ($AgNO_3$) and the like. Alternatively, the silver-containing precursor can be soluble in an organic solvent. Suitable palladium-containing precursor compounds include palladium nitrate ($Pd(NO_3)_2$) and the like. Suitable palladium-containing precursor compounds soluble in an organic solvent include palladium dioxide ($PdO_2$), which is soluble in acetone, and the like.

The catalyst support material impregnated with a catalytic metal or a compound thereof and optionally a promoter or a compound thereof can be further treated to form the catalyst material. Such treatment can include drying the impregnated support. Drying preferably occurs at a temperature between about 80° C. and about 150° C. Typically, drying proceeds for from about 0.5 to about 24 hours at a pressure of from about 1 to about 75 atm, more preferably from about 1 to about 10 atm, most preferably at about 1 atm.

Alternatively or in combination to drying, the treatment can include calcining (e.g., calcining the impregnated support). The calcination desirably achieves conversion of any impregnated decomposable compound or salt of a catalyst material to an oxide form of the catalyst material on the stabilized support, for example conversion of the impregnated salt of a catalytic metal to an oxide form. For example and by no limitation, when the catalytic metal includes cobalt impregnated as a decomposable salt of cobalt, the calcination preferably proceeds at a temperature of at least about 200° C. Further, the calcination of the catalyst precursor preferably proceeds at a temperature less than the temperature at which loss of support surface area is appreciable. It is believed that, at temperatures above 900° C., loss of support surface area is appreciable. When the catalytic metal includes cobalt, the calcination temperature preferably ranges from about 200° C. to about 900° C. In some embodiments, the calcination of a catalyst precursor which includes cobalt is performed at a calcination temperature from about 350° C. to about 800° C., or from about 450° C. to about 800° C., or from about 450° C. to about 755° C. In alternate embodiments, the calcination of a cobalt-containing material is performed at a calcination temperature from about 200° C. to about 450° C., or from about 210° C. to about 425° C., or from about 215° C. to about 400° C. or from about 215 to about 400° C., or from about 220° C. to about 325° C. Typically, calcining proceeds from about 0.5 to about 24 hours at a pressure of about 0.01 to about 75 atm, more preferably from about 1 to about 10 atm, most preferably at about 1 atm. When the preparation of the catalyst includes a multi-step impregnation of a catalytic metal on the catalyst support material, calcination may be performed after each impregnation of the catalytic metal-containing compound and optionally of the promoter-containing compound, or it may be performed after all impregnations have been completed. However, in certain embodiments, any calcining step of the catalyst precursor after any impregnation following the first calcination desirably proceeds at a temperature of not more than about 500° C., or not more than about 450° C., or not more than about 350° C.

Calcining at a pressure of about 100 kPa or higher is desirable. The calcining can be performed at pressures from about 0 to about 500 kPa (about 0 to about 5 atm), more preferably from about 100 to about 500 kPa (about 1 atm to about 5 atm), most preferably from about 100 to about 105 kPa (about 1 atm).

The impregnation of catalytic metal and any optional promoter on the support can proceed by multi-step impregnation, such as by two, three, or four impregnation steps. Each impregnation step can include impregnation of any one or combination of a catalytic metal and promoter. Each impregnation step can be followed by any of the above-described treatments of the impregnated support. Thus, a multi-step impregnation can include multiple steps of drying and/or calcination. Each subsequent step of drying can proceed at a different temperature from any earlier steps of drying. Further, each subsequent step of calcination can proceed at a different temperature than the temperature used in any earlier steps of calcination. By way of example and not limitation, a multi-step impregnation can include calcining the support at a first temperature that is higher than the temperature for subsequent calcinations.

The impregnation, drying, and calcination steps may be repeated, for example, until the desired catalytic metal loading is obtained. Each impregnation step may include impregnation of any one or combination of catalytic metal-containing compound and promoter-containing compound. Each subsequent step of drying may proceed at a different temperature from any earlier steps of drying. Further, each subsequent step of calcination may proceed at a different temperature from any earlier steps of calcination.

Calcined catalytic materials will generally include a catalytic metal oxide on the catalyst support material. Such materials may be ready to use in a catalytic process if the process can proceed with the oxide, or if the oxide would be activated to an active form during the catalytic process (e.g., an in situ reduction step in a reactor vessel in which it is to be used).

In certain embodiments, the catalyst precursor can be activated before use. For example, for use in a Fischer-Tropsch process, the catalyst metal can be reduced to a substantially metallic state via a reduction treatment in the presence of a reducing gas at an elevated temperature.

In one embodiment, at least a portion of the metal(s) of the catalytic metal component of the catalyst material may be present in a reduced state (i.e., in the metallic state). Therefore, it may be advantageous to activate the catalyst prior to use by a reduction treatment in the presence of a reducing gas at an elevated temperature. The reducing gas desirably includes hydrogen. Typically, the catalyst material is treated with hydrogen or a hydrogen-containing gas at a temperature in the range of from about 75° C. to about 500° C., for about 0.5 to about 50 hours at a pressure of about 1 to about 75 atm, preferably at a pressure of about 1 to about 10 atm. Pure hydrogen can be used in the reduction treatment. Moreover, a mixture of hydrogen and an inert gas such as nitrogen or a mixture of hydrogen and other suitable gases, such as carbon monoxide and carbon dioxide, can be used in the reduction treatment. Reduction with pure hydrogen and reduction with a mixture of hydrogen and carbon monoxide are preferred. The amount of hydrogen may range from about 1% to about 100% by volume.

The metal catalyst described above may be used to facilitate any reaction requiring a reduced metal catalyst. That is, the catalyst may be used with various reactants to promote the production of different products. In some embodiments, the catalyst described above is used in a Fischer-Tropsch process for producing synthesis gas or for synthesizing hydrocarbons and/or alcohols, depending especially on the identity and state of the catalytic metal.

Another aspect of the disclosure is a process for producing one or more hydrocarbons, e.g., by the Fischer-Tropsch reaction. One embodiment of such a process includes contacting carbon monoxide and hydrogen with a catalyst material as described herein.

Mixtures of hydrogen and carbon monoxide suitable as a feedstock for conversion to hydrocarbons according to the processes described herein can be obtained from light hydrocarbons such as methane by means of steam reforming, partial oxidation, or other processes known in the art. Desirably, the hydrogen is provided in the feedstock as free hydrogen, although some Fischer-Tropsch catalyst materials have sufficient water gas shift activity to convert some water and carbon monoxide to hydrogen and carbon dioxide, thus producing hydrogen in situ for use in the Fischer-Tropsch process. In certain embodiments, the molar ratio of hydrogen to carbon monoxide when contacted with the catalyst material greater than 0.5:1 (e.g., from about 0.67 to 2.5). In certain embodiments, for example, when cobalt, nickel, and/or ruthenium catalysts are used, the hydrogen and carbon monoxide are present in a molar ratio of about 1.6:1 to 2.3:1, when contacted with the catalyst material. In certain embodiments, for example, when iron catalysts are used, the hydrogen and carbon monoxide are present in a molar ratio of about 1.4:1 and 2.3:1, when contacted with the catalyst material. As the person of ordinary skill in the art will appreciate, various other substances can be present, such as water, carbon dioxide, and/or hydrocarbonaceous products of the Fischer-Tropsch reaction. Desirably, only a low concentration (if any) compounds or elements that have a deleterious effect on the catalyst, such as poisons, should be present. For example, the feed gas may need to be pretreated to ensure that it contains low concentrations of sulfur or nitrogen compounds such as hydrogen sulfide, ammonia, hydrogen cyanide, and carbonyl sulfides.

The carbon monoxide and the hydrogen can be contacted with the catalyst material in a reaction zone. As the person of ordinary skill in the art will appreciate, the reaction zone can take many physical forms. Mechanical arrangements of conventional design may be employed as the reaction zone including, for example, plug flow, continuous stirred tank, fixed bed, fluidized bed, slurry phase, slurry bubble column, reactive distillation column, or ebulliating bed reactors, among others. The size and physical form of the catalyst may vary, depending on the reactor in which it is to be used. Plug flow, fluidized bed, reactive distillation, ebulliating bed, and continuous stirred tank reactors have been delineated in "Chemical Reaction Engineering," by Octave Levenspiel, and are known in the art, as are slurry bubble column. In one particular embodiment, the reaction zone is a slurry bubble column. One particular slurry bubble column is described in United States Patent Application Publication 2003/0114543, which is hereby incorporated herein by reference in its entirety.

When the reaction zone includes a slurry bubble column, the column can include, for example, a three-phase slurry (i.e., a solid phase including at least the catalyst material; a liquid phase including at least a hydrocarbon fluid; and a gas phase including at least the carbon monoxide and the hydrogen). For example, a process as described herein performed in a slurry bubble column preferably includes dispersing the particles of the catalyst in a liquid phase including the hydrocarbons to form a two-phase slurry and dispersing the hydrogen and carbon monoxide in the two-phase slurry to form the three-phase slurry. The slurry bubble column can include, for example, a vertical reactor, and dispersal desirably includes injection of the gas into the bottom half of the reactor.

The Fischer-Tropsch process may be typically run in a continuous mode. In this mode, the gas hourly space velocity through the reaction zone can range, for example, from about 50 to about 10,000 $hr^{-1}$, or from about 300 $hr^{-1}$ to about 2,000 $hr^{-1}$. The gas hourly space velocity is defined as the volume of reactants per time per reaction zone volume. The volume of reactant gases is determined at (or extrapolated to) standard conditions (standard pressure of 101 kPa and standard temperature of 0° C.). The reaction zone volume is defined by the portion of the reaction vessel volume where the reaction takes place and which is occupied by a gaseous phase comprising reactants, products and/or inerts; a liquid phase comprising liquid/wax products and/or other liquids; and a solid phase comprising the catalyst material. The temperature at which the hydrogen and carbon monoxide are contacted with the catalyst material (e.g., the reaction zone temperature) may vary, as would be apparent to the person of ordinary skill in the art. For example, the temperature at which the hydrogen and carbon monoxide are contacted with the catalyst material (e.g., the reaction zone temperature) may be in the range from about 160° C. to about 300° C.; or from about 190° C. to about 260° C., or from about 205° C. to about 230° C. The pressure at which the contacting of the hydrogen and carbon monoxide with the catalyst material (e.g., the reaction zone pressure) is performed can be, for example, in the range of about 80 psia (552 kPa) to about 1000 psia (6,895 kPa), or from 80 psia (552 kPa) to about 800 psia (5,515 kPa), or from about 140 psia (965 kPa) to about 750 psia (5,170 kPa), or from about 250 psia (1,720 kPa) to about 650 psia (4,480 kPa).

The products resulting from the process may have a great range of molecular weights. Typically, the carbon number range of the product hydrocarbons may start at methane and continue to about 50 to 100 carbons or more per molecule as measured by current analytical techniques. The process is particularly useful for making hydrocarbons having five or more carbon atoms, especially when the above-referenced preferred space velocity, temperature and pressure ranges are employed.

Typically, in the Fischer-Tropsch synthesis, the product spectra can be described by likening the Fischer-Tropsch reaction to a polymerization reaction with a Shultz-Flory chain growth probability, called alpha value (a), that is independent of the number of carbon atoms in the lengthening molecule. The alpha value is typically interpreted as the ratio of the mole fraction of the $C_{n+1}$ product to the mole fraction of the $C_n$ product. An alpha value of at least 0.72 is desirable for producing high carbon-length hydrocarbons, such as those of diesel cuts.

The wide range of hydrocarbons produced can afford liquid phase products under the reaction conditions. Therefore, the effluent stream of process may be a mixed phase stream including liquid and gas phase products. The effluent gaseous stream of the reaction zone can be cooled to condense additional amounts of hydrocarbons and can be passed into a vapor-liquid separation zone separating the liquid and vapor phase products. The gaseous material can be passed into a second stage of cooling for recovery of additional hydrocarbons. The liquid material from the reaction zone together with any liquid from a subsequent separation zone can be fed into a fractionation column. In an embodiment, a stripping column is employed first to remove light hydrocarbons such as propane and butane. The remaining hydrocarbons can be passed into a fractionation column in which they are separated by boiling point range into products such as naphtha, kerosene and fuel oils. Hydrocarbons recovered from the reaction zone and having a boiling point above that of the desired products can be passed into conventional processing equipment such as a hydrocracking zone in order to reduce their molecular weight to that of desired products such as middle distillates and gasoline. The gas phase recovered from the reactor zone effluent stream after hydrocarbon recovery can be partially recycled if it contains a sufficient quantity of hydrogen and/or carbon monoxide.

Various aspects of the disclosure are further described via the Example preparations described below:

A spray-dried alumina/silicon oxide composition having 6 wt % $SiO_2$ was provided. Tetraethylorthosilicate was impregnated onto an alumina (T-2865) spray-dried carrier. After drying, the TEOS-impregnated material was rotary calcined at a bed temperature of 1380° F. to convert the boehmite to gamma alumina. 11.35 kg was obtained. LOD (250° F.) 0.18%, LOI (1000° F.) 1.61%, water pickup 58.55%.

The calcined alumina/silicon oxide composition was then impregnated with a titanium oxide precursor. 4117.77 grams of Tyzor® LA (aqueous titanium lactate solution (13.8 wt % $TiO_2$), Dupont) were weighed in a 2-gallon plastic bucket.

Deionized water was added to a total volume of 4420 mL. 7561.87 grams of calcined alumina/silicon oxide composition were loaded into a pilot plant cement mixer. The Tyzor® LA solution was pumped into the mixing alumina/silicon oxide composition at a rate of 500 mL/min. The impregnated material was discharged into a plastic bag.

The impregnated material was dried in the pilot plant rotary with a furnace temperature of 250° F. and a bed temperature of about 185° F. The dried material was then rotary calcined at a bed temperature of about 1100° F. to form a catalyst support material. Yield 7.50 kg, LOI (1000° F.) 1.26%, water pickup 53.77%.

A first Co/Pt impregnation process was then performed. 5000.2 grams of cobalt nitrate crystals (20 wt % Co, Shepherd Chemicals) were dissolved in deionized water and 62.4067 grams of tetraammine platinum(II) nitrate solution (2 wt % Pt, Colonial Metals Inc.) were added. The solution volume was adjusted to 3950 mL with deionized water. 7342.2 grams of the catalyst support material were loaded into a cement mixer and the Co/Pt solution was impregnated onto the mixing carrier with a peristaltic pump at a rate of 500 mL/min. The impregnated material was rotary dried with a furnace temperature of 250° F. and a bed temperature of about 185° F. The dried material was rotary calcined at a bed temperature of about 460° F. LOI (1000° F.) 3.98%, water pickup 42.39%.

The Co/Pt impregnation process as described above was repeated, using 4399.48 grams of cobalt nitrate crystals, 27.4597 grams of tetraammine platinum(II) nitrate solution (5 wt % Pt, Colonial Metals Inc.)) at 3600 mL total volume and 8500 grams of calcined material from the 1st impregnation. The impregnated material was dried and calcined using the same procedure from the 1st impregnation. Yield 9.45 kg, LOI (1000° F.)3.74%, water pickup 37.47%.

The Co/Pt impregnation process as described above was repeated, using 3781.8 grams of cobalt nitrate crystals, 23.5982 grams of tetraammine platinum(II) nitrate solution (5% wt % Pt) at 3500 mL total volume and 9450 grams of calcined material from the $2^{nd}$ impregnation. The impregnated material was dried and calcined using the same procedure from the $1^{st}$ impregnation. Yield 10.2 kg.

The calcined material from the 3rd impregnation was rotary calcined at a bed temperature of about 660° F. to denitrate it. Yield 10.0 kg, LOI (1000° F.)3.57%, XRD: Co3O-1 (188 A), Co 25.14%, Pt 391 ppm, Ti 2.86% (all on oxide basis), surface area 72 m²/g, pore volume 0.20 mL/g, average pore diameter 108 Å.

Using similar procedures, analogous materials having 3.0% or 7.0% titanium dioxide, 25% cobalt and 390 ppm platinum (all on an oxide basis) were also prepared.

Comparative studies were performed between Co/Pt catalysts using three different carriers: T-2865 alumina, T-2865 alumina impregnated with 6% $SiO_2$, and a material of the present disclosure (T-2865 alumina impregnated with 6% $SiO_2$ and 3% $TiO_2$). Long-term performance in a Fischer-Tropsch process in a bubble column reactor is shown in FIG. 1. As shown in FIG. 1, the reactions were performed under similar(although not identical) conditions, Notably, the long-term performance of the catalyst of the present disclosure was much greater than the catalysts using T-2865/6% $SiO_2$ and T-2865 as the carrier.

I claim:

1. A catalyst material comprising a catalyst support material and one or more catalytic metals disposed on the catalyst support material, the one or more catalytic metals including cobalt, the catalyst support material comprising in the range of about 75 wt% to about 96 wt% gamma-alumina, calculated as $Al_2O_3$ on an oxide basis, in the range of about 1 wt% to about 20 wt% silicon oxide, calculated as $SiO_2$ on an oxide basis and in the range of about 1 wt% to about 20 wt% titanium dioxide, calculated as $TiO_2$ on an oxide basis, wherein the silicon oxide and gamma-alumina are provided as a substantially non-homogeneous mixture in which the silicon oxide is not homogeneously mixed throughout the gamma-alumina and in which the gamma-alumina is substantially enveloped by the silicon oxide; or the silicon oxide is dispersed in the gamma-alumina as a dispersed silicon oxide phase, as a dispersed phase of a silicon aluminate, or as a combination thereof, the gamma-alumina and the silicon oxide are substantially coated by the titanium dioxide, and at least about 90 wt% of the catalyst support is gamma-alumina, silicon oxide and titanium dioxide.

2. The catalyst material according to claim 1, wherein the gamma-alumina is substantially enveloped by the silicon oxide.

3. The catalyst material according to claim 1, comprising in the range of about 1 wt% to about 13 wt% silicon oxide, calculated as $SiO_2$ on an oxide basis.

4. The catalyst material according to claim 1, wherein the titanium dioxide is substantially amorphous, substantially in a rutile phase, or a mixture of the two.

5. The catalyst material according to claim 1, comprising in the range of about 1 wt% to about 13 wt% titanium dioxide, calculated as $TiO_2$ on an oxide basis.

6. The catalyst material according to claim 1, wherein the catalyst support material is in the form of a plurality of discrete porous particles, in which the discrete particles have an average discrete particle size in the range of about 10 μm to about 150 μm;

the catalyst support material has an average pore size in the range of about 4 nm to about 50 nm;

the catalyst support material has a pore volume within the range of about 0.05 to about 1 cm³/g; and the catalyst support material has a surface area within the range of from about 10 to about 300 m²/g.

7. A catalyst material according to claim 1, wherein the total amount of the catalytic metal(s) and any promoters is in the range of about 1 wt% to about 70 wt% of the total catalyst material.

8. A catalyst material according to claim 1, wherein the one or more catalytic metals are present in the form of one or more metal oxides.

9. A catalyst material according to claim 1, wherein the one or more catalytic metals are present in the form of one or more substantially reduced metals.

10. A catalyst material according to claim 1, comprising in the range of about 1 wt% to about 13 wt% silicon oxide; and in the range of about 1 wt% to about 13 wt% titanium dioxide, substantially amorphous or in rutile phase.

11. The catalyst material according to claim 10, wherein the gamma-alumina is substantially enveloped by the silicon oxide.

12. A catalyst material according to claim 1, wherein the catalyst material further comprises one or more of platinum, ruthenium, rhenium, silver and boron.

13. The catalyst material according to claim 1, wherein at least about 95 wt% of the catalyst support is gamma-alumina, silicon oxide and titanium dioxide.

14. The catalyst material according to claim 1, wherein cobalt is present in an amount in the range of 10 wt% to 37 wt% on an oxide basis.

15. A process for producing one or more hydrocarbons, the process comprising contacting carbon monoxide and hydrogen with a catalyst material according to claim 1.

16. A process according to claim 15, wherein
the molar ratio of hydrogen to carbon monoxide is in the range of about 0.67 to about 2.5;
the process is performed with a gas hourly space velocity in the range of about 50 to about 10,000 $hr^{-1}$;
the temperature at which the hydrogen and carbon monoxide are contacted with the catalyst material is in the range from about 160° C. to about 300° C.; and
the pressure at which the contacting of the hydrogen and carbon monoxide with the catalyst material is performed is in the range of about 80 psia (552 kPa) to about 1000 psia (6,895 kPa).

* * * * *